(12) United States Patent
Boldingh et al.

(10) Patent No.: US 7,566,810 B2
(45) Date of Patent: *Jul. 28, 2009

(54) XYLENE PRODUCTION PROCESSES EMPLOYING RHENIUM-CONTAINING CATALYSTS

(75) Inventors: Edwin P. Boldingh, Arlington Heights, IL (US); Antoine Negiz, Wilmette, IL (US); James E. Rekoske, Glenview, IL (US); Eric J. Baker, Romeoville, IL (US); Robert B. Larson, Lisle, IL (US); Terrence E. Deak, Chicago, IL (US); Sergey V. Gurevich, San Mateo, CA (US)

(73) Assignee: UOP LLC, Des Plaines, IL (US)

( * ) Notice: Subject to any disclaimer, the term of this patent is extended or adjusted under 35 U.S.C. 154(b) by 76 days.

This patent is subject to a terminal disclaimer.

(21) Appl. No.: 11/843,718

(22) Filed: Aug. 23, 2007

(65) Prior Publication Data

US 2008/0064910 A1    Mar. 13, 2008

Related U.S. Application Data

(60) Provisional application No. 60/825,306, filed on Sep. 12, 2006, provisional application No. 60/825,313, filed on Sep. 12, 2006.

(51) Int. Cl.
*C07C 6/12* (2006.01)
(52) U.S. Cl. ....................................................... 585/475
(58) Field of Classification Search .................. 585/475
See application file for complete search history.

(56) References Cited

U.S. PATENT DOCUMENTS

| | | | | |
|---|---|---|---|---|
| 3,562,345 A | 2/1971 | Mitsche | ........................ | 260/672 |
| 3,646,236 A | 2/1972 | Keith et al. | ............... | 260/672 T |
| 4,183,827 A | 1/1980 | Adams et al. | ................ | 252/439 |
| 4,341,914 A | 7/1982 | Berger | ......................... | 585/474 |
| 4,857,666 A | 8/1989 | Barger et al. | ................ | 585/323 |
| 5,004,855 A | 4/1991 | Tada et al. | ................... | 585/489 |
| 5,763,720 A | 6/1998 | Buchanan et al. | ........... | 585/475 |
| 5,847,256 A | 12/1998 | Ichioka et al. | ............... | 585/470 |
| 5,942,651 A | 8/1999 | Beech, Jr. et al. | ........... | 585/475 |
| 5,952,536 A | 9/1999 | Nacamuli et al. | ........... | 585/475 |
| 5,993,642 A | 11/1999 | Mohr et al. | .................... | 208/46 |
| 6,060,417 A | 5/2000 | Kato et al. | .................... | 502/66 |
| 6,359,184 B1 | 3/2002 | Kato et al. | ................... | 585/321 |
| 6,613,709 B1 | 9/2003 | Merlen et al. | ................. | 502/64 |
| 6,815,570 B1 | 11/2004 | Negiz et al. | ................. | 585/475 |
| 6,867,340 B2 | 3/2005 | Oh et al. | ..................... | 585/475 |
| 6,872,866 B1 | 3/2005 | Nemeth et al. | ............... | 585/481 |
| 6,958,425 B1 | 10/2005 | Bogdan et al. | .............. | 585/323 |
| 6,972,347 B1 | 12/2005 | Kitamura et al. | ............ | 585/475 |
| 6,972,348 B2 | 12/2005 | Negiz et al. | ................. | 585/475 |
| 7,148,391 B1 | 12/2006 | Buchanan et al. | ........... | 585/475 |
| 7,179,434 B1 | 2/2007 | Maher et al. | ................. | 422/236 |
| 7,202,189 B2 | 4/2007 | Negiz et al. | ................... | 502/74 |
| 7,220,885 B2 | 5/2007 | Boldingh et al. | ............. | 585/475 |
| 7,230,152 B1 | 6/2007 | Boldingh | ..................... | 585/470 |
| 2005/0215838 A1 | 9/2005 | Negiz et al. | ................. | 585/475 |
| 2005/0266979 A1 | 12/2005 | Boldingh et al. | .............. | 502/64 |
| 2006/0182681 A1 | 8/2006 | Kumar et al. | ................ | 423/700 |

OTHER PUBLICATIONS

Lee et al., The influence of mordenite characteristics in mordenite mixed with alumina on cracking of vacuum gas oil. Korean J. Chem. Eng. 1997.
Meyers, R.A., Part 2, Handbook of Petroleum Refining Processes, 2nd Edition, McGraw-Hill, 1997, pp. 2.1-2.62 ISBN 0-07-041796-2.
USPTO Office Action dated May 30, 2008 in U.S. Appl. No. 11/843,719, filed Aug. 23, 2007.
Applicants' Response and Terminal Disclaimer dated Sep. 2, 2008 in U.S. Appl. No. 11/843,719.
USPTO Notice of Allowance dated Sep. 28, 2008 in U.S. Appl. No. 11/843,719, filed Aug. 23, 2007.

*Primary Examiner*—Thuan Dinh Dang
(74) *Attorney, Agent, or Firm*—David J Piasecki

(57) ABSTRACT

Processes for making xylene employ catalysts containing rhenium and a molecular sieve component comprising an acidic MFI molecular sieve having a $Si/Al_2$ molar ratio of less than about 80 and mordenite to provide a transalkylation product with a low content of benzene co-boilers. The invention encompasses the use of sulfided catalyst embodiments in xylene production processes.

20 Claims, No Drawings

XYLENE PRODUCTION PROCESSES EMPLOYING RHENIUM-CONTAINING CATALYSTS

CROSS-REFERENCE TO RELATED APPLICATION

This application claims priority from Provisional Application Nos. 60/825,306 and 60/825,313 both of which were filed on Sep. 12, 2006, and each is hereby incorporated by reference in its entirety.

FIELD OF THE INVENTION

This invention relates to improved catalysts, processes for preparing the catalysts, and processes for transalkylating alkylaromatics employing the catalysts. The catalysts contain an acidic MFI molecular sieve component having a $Si/Al_2$ molar ratio of less than 80, a mordenite component, a rhenium component, a rhenium-dispersing binder and optionally a sulfur component to provide a desirable transalkylation product having a low benzene co-boiler content. The catalysts are also suitable for the disproportionation of toluene and the dealkylation of ethyl and higher alkyl groups of alkylbenzenes such as methyl ethyl benzene.

BACKGROUND OF THE INVENTION

The xylene isomers are produced in large volumes from petroleum as feedstocks for a variety of important industrial chemicals. The most important of the xylene isomers is para-xylene, the principal feedstock for polyester, which continues to enjoy a high growth rate from large base demand. Ortho-xylene is used to produce phthalic anhydride, which supplies high-volume but relatively mature markets. Meta-xylene is used in lesser but growing volumes for such products as plasticizers, azo dyes and wood preservers. A prior art aromatics complex flow scheme has been disclosed by Meyers in Part 2 of the Handbook of Petroleum Refining Processes, Second Edition, 1997, published by McGraw-Hill.

In general, a xylene production facility can have various types of processing reactions. One is a transalkylation in which benzene and/or toluene are reacted with $C_9^+$ aromatics to form xylene. Another is xylene isomerization, which may also include dealkylation, where a non-equilibrium mixture of xylenes is isomerized. And another is the disproportionation of toluene to form benzene and xylene.

In the transalkylation process, adverse side reactions can occur. For instance, the aromatic ring may become saturated or even cleaved resulting in naphthene and acyclic paraffin (non-aromatics) co-production. The co-production of these non-aromatics, of course, results in a loss of valuable aromatics. Moreover, benzene is often a sought co-product from a xylene production facility. As some of the non-aromatics have similar boiling points to benzene (benzene co-boilers), they are not readily removed to achieve a benzene product of sought purity for commercial applications which frequently demand a benzene product having at least a 99.85 percent purity.

U.S. Pat. No. 3,562,345 discloses catalysts for transalkylation or disproportionation of alkylaromatics comprising aluminosilicates such as mordenite. Catalytically active metals such as groups VIB and VIII metals may be present.

U.S. Pat. No. 4,857,666 discloses a transalkylation process over mordenite and suggests modifying the mordenite by steam deactivation or incorporating a metal modifier into the catalyst.

U.S. Pat. No. 5,004,855 discloses a catalyst for dealkylating ethylbenzene containing a hydrogenation metal such as platinum, nickel or rhenium and acidic zeolite. They state that the catalyst is subjected to a sulfiding treatment before use. While they state that any method capable of converting rhenium to a sulfide can be adopted for the sulfiding treatment, they prefer sulfiding with hydrogen sulfide at a temperature between room temperature and 500° C. The sulfiding treatment can be carried out in a reaction vessel just before use or before the calcination for activation in air. By sulfiding, the activity of the catalyst is purported to be increased and the loss of xylene due to the side reaction is said to be decreased.

U.S. Pat. No. 5,763,720 discloses a transalkylation process for conversion of $C_9+$ aromatics over a catalyst containing zeolites illustrated in an extensive list including amorphous silica-alumina, MCM-22, ZSM-12, and zeolite beta, where the catalyst further contains a Group VIII metal such as platinum.

U.S. Pat. No. 5,942,651 discloses a transalkylation process in the presence of two zeolite containing catalysts. The first zeolite catalyst is selected from the group consisting of MCM-22, PSH-3, SSZ-25, ZSM-12, and zeolite beta. The second zeolite catalyst contains ZSM-5, and is used to reduce the level of saturated co-boilers in making a higher purity benzene product.

U.S. Pat. No. 5,952,536 discloses a transalkylation process using a catalyst comprising a zeolite selected from the group consisting of SSZ-26, A1-SSZ-33, CIT-1, SSZ-35, and SSZ-44. The catalyst also comprises a mild hydrogenation metal such as nickel or palladium, and can be used to convert aromatics with at least one alkyl group including benzene.

U.S. Pat. No. 5,847,256 discloses a process for producing xylene from a feedstock containing $C_9$ alkylaromatics with ethyl-groups over a catalyst containing a zeolite component that is preferably mordenite and with a metal component that is preferably rhenium.

U.S. Pat. No. 6,060,417 discloses catalysts and processes for transalkylation of alkylaromatics wherein the catalysts comprise mordenite, inorganic oxide and/or clay and at least one metal component of rhenium, platinum and nickel. See also, U.S. Pat. No. 6,359,184.

U.S. Pat. No. 6,867,340 discloses disproportionation/transalkylation catalysts having a carrier and a metal component on the carrier. The metal component is platinum and either tin or lead, and the carriers comprise mordenite and/or beta zeolite with certain $Al/Si_2$ ratios, optionally ZSM-5 zeolite with certain $Al/Si_2$ ratios, and binder. The benefits of the catalyst are said to be high yields of xylenes and preventing catalyst deactivation.

U.S. Pat. No. 6,872,866 discloses a liquid phase xylene isomerization process which uses a zeolite beta and pentasil-type zeolite. The catalyst can contain a hydrogenation metal component such as a platinum group metal and modifiers such as rhenium, tin, germanium, lead, cobalt, nickel, indium, gallium, zinc, uranium, dysprosium, thallium, and mixtures thereof.

US Patent Application Publication No. 2005/0026771, now U.S. Pat. No. 7,202,189, discloses catalysts for transalkylation of $C_7$, $C_9$, and $C_{10}$ aromatics to $C_8$ aromatics having a trilobe shape with a maximum effective diameter of 0.16 cm. The catalyst is composed of a support, which can be selected from the group consisting of mordenite, beta, MFI, silica-alumina and mixtures thereof. The catalyst is also composed of an optional element deposited on the support selected from the group consisting of platinum, tin, lead, indium, germanium, rhenium, or any combination of these elements. The catalyst also can contain a binder, which is preferably alumina. The preferred support is mordenite.

US Patent Application Publication No. 2005/0266979, now U.S. Pat. No. 7,220,885, discloses catalysts having a sulfur component, a rhenium component, and a solid-acid component for transalkylation processes to convert aromatics into xylenes with decreased methane production. The catalysts have a solid-acid component such as mordenite, mazzite, zeolite beta, ZSM-11, ZSM-12, ZSM-22, ZSM-23, MFI topology zeolite, NES topology zeolite, EU-1, MAPO-36, MAPSO-31, SAPO-5, SAPO-11, SAPO-41, and silica-alumina. The sulfur component may be incorporated into the catalyst by any known technique. Any one or a combination of in situ and/or ex situ sulfur treatment methods is preferred. The resulting catalyst mole ratio of sulfur to rhenium is preferably from about 0.1 to less than about 1.5. In ex situ sulfiding, the catalyst is contacted with a source of sulfur at a temperature ranging from about 0° to about 500° C. The source of sulfur, typically hydrogen sulfide, can be contacted with the catalyst directly or via a carrier gas, typically, an inert gas such as hydrogen or nitrogen. The catalyst composition can also be treated in situ where a source of sulfur is contacted with the catalyst composition by adding it to the hydrocarbon feed stream in a concentration ranging from about 1 ppm-mole sulfur to about 10,000 ppm-mole sulfur. Typical examples of appropriate sources of sulfur include carbon disulfide and alkylsulfides such as methylsulfide, dimethylsulfide, dimethyldisulfide, diethylsulfide and dibutylsulfide.

Mordenite, due to its high transalkylation activity, has found application as a catalyst component for transalkylation processes. The addition of rhenium as a hydrogenation component has greatly enhanced the performance of the catalyst in transalkylation processes. Under transalkylation conditions, ethyl substituents from, e.g., methylethylbenzene, are typically cleaved from the aromatic ring and should be hydrogenated to ethane. One of the problems is that the reaction must be selective. Thus, the hydrogenation should be sufficient to convert an ethylene to ethane yet not result in hydrogenation of the aromatic ring. Heretofore transalkylation catalysts have used relatively small amounts of rhenium, generally up to about 0.2 mass percent, in order to achieve a balance between hydrogenation activity and the avoidance of Ring Loss. The low metal loading, however, results in a catalyst that has a higher deactivation rates than desired, especially with feeds containing aromatics of 10 or more carbons. Feeds containing these higher alkylaromatics are advantageous in order to recover more xylene values from a xylene production unit. Other molecular sieves including MFI have been suggested for transalkylation. Accordingly, a need exists for catalysts and processes for the transalkylation of alkylaromatics, which processes have desirable activities and selectivities of conversion to the desired alkylaromatics such as xylenes, yet result in low Ring Loss, have improved stability, and provide a benzene co-product having a low content of benzene co-boilers, i.e., a low content of non-aromatics having 6 and 7 carbon atoms.

DEFINITIONS

Evaluation Conditions are:

| Feedstock (+/−0.5%-mass): | |
|---|---|
| Toluene: | 75%-mass |
| Trimethylbenzene: | 10%-mass |
| Methylethylbenzene: | 10%-mass |
| Propylbenzene: | 2%-mass |
| Dimethylethylbenzene: | 1%-mass |

| -continued | |
|---|---|
| Feedstock (+/−0.5%-mass): | |
| Diethylbenzene: | 0.5%-mass |
| Tetramethylbenzene: | 0.5%-mass |
| Other alkylaromatics and benzene: | balance |
| Pressure: | 1725 kPa (absolute) |
| WHSV, hr$^{-1}$: | 4 |
| H$_2$/HC: | 6 |
| Overall Conversion: | 30%-mass |

As used herein, when values are stated as "ranges", "ranging", "between" and the like, the values include the end points given. H$_2$/HC is the hydrogen to hydrocarbon mole ratio. Overall conversion is the weighted average conversion of the compounds in the feed. Ring Loss, expressed as mole percent, is determined as the difference between the moles of monocyclic aromatic rings in the feed to the transalkylation reactor and the moles of monocyclic aromatic rings in the effluent from the transalkylation reactor relative to the moles of monocyclic aromatic rings in the feed. MCP Index is the ratio of methylcyclopentane in the product to the methylcyclopentane in the feed expressed as a percent based upon the conversion of methylcyclopentane in a feed containing about 0.1 mass percent methylcyclopentane in benzene at 380° C. in the presence of the catalyst at 1725 kPa (absolute), a weight hourly space velocity (WHSV) of 4 hr$^{-1}$, and a hydrogen to methylcyclopentane mole ratio of 6.

SUMMARY OF THE INVENTION

In accordance with the invention, rhenium-containing catalysts are provided that exhibit desirable activities and selectivities for the transalkylation of alkylaromatics with relatively low co-production of non-aromatic benzene co-boilers. As used herein, the term transalkylation is intended to include transalkylation between and among alkylaromatics as well as between benzene and alkylaromatics and includes disproportionation, e.g., of toluene to benzene and xylene. In an embodiment the transalkylation catalyst comprises a mordenite component; an acidic MFI molecular sieve component having a Si/Al$_2$ molar ratio of less than about 80; a rhenium component; and a rhenium-dispersing binder. In another embodiment the transalkylation catalyst further comprises a sulfur component wherein the atomic ratio of sulfur to rhenium is between about 0.2:1 and about 0.7:1. Such catalysts provide not only desirable overall conversion, but also low benzene co-boilers make. Moreover, the catalysts of this invention can provide enhanced stability and xylene yields during transalkylations to xylenes especially where the feed for transalkylation contains trimethylbenzene and methylethylbenzene.

The invention, in an embodiment, is a process for making a transalkylation catalyst comprising forming the catalyst comprising a mordenite component, an acidic MFI molecular sieve component having a Si/Al$_2$ molar ratio of less than about 80, a rhenium component, and a rhenium-dispersing binder; oxidizing the formed catalyst at conditions including an oxygen atmosphere, a temperature of between 370° C. and about 650° C., and a time of between about 0.5 and about 10 hours; and reducing the oxidized catalyst in a gas comprising hydrogen at conditions including a temperature between about 100° C. and about 650° C. Where the catalyst contains sulfur, the sulfur may be added by any well known technique preferably at a temperature between about 0° C. and 500° C. to provide a an atomic ratio of sulfur to rhenium between about 0.2:1 and about 0.7:1. In an embodiment, sulfur ranging from about 1 to about 10,000 ppm-mole is added to the reduction gas during reduction of the oxidized catalyst. In another embodiment, this reduction/sulfiding step is conducted between about 200° C. to about 400° C. with a hydrocarbon in the reduction gas.

In an embodiment, the invention is a process for producing xylene comprising contacting a feed stream comprising an aromatic hydrocarbon having at least seven carbon atoms with a catalyst at aromatic conversion conditions including the presence of hydrogen wherein the catalyst comprises a mordenite component; an acidic MFI molecular sieve component having a $Si/Al_2$ molar ratio of less than about 80; a rhenium component; and a rhenium-dispersing binder; and producing a product stream having an increased concentration of xylene.

DETAILED DESCRIPTION OF THE INVENTION

Processes for Use

Transalkylation

The processes of this invention comprise transalkylation between lighter (non- or less substituted) aromatics and heavier, greater substituted alkylaromatics with the product being alkylaromatics having the number of substitutions between those of the lighter fraction and those of the heavier fraction and disproportionation of a substituted aromatic to provide a greater substituted aromatic and a lesser substituted aromatic, e.g., the disproportionation of toluene to form xylene and benzene. The lighter aromatics have 0 to 2 substituents and the heavier aromatics have 2 to 5 substituents with the product falling in between. For example, benzene may be transalkylated with methylethylbenzene to provide toluene and ethylbenzene. Similarly, benzene or toluene may be transalkylated with trimethylbenzene to provide xylene. In some instances for xylene production facilities, it may be desired to consume benzene in the transalkylation rather than producing it as a co-product in which case benzene may comprise from 5 to 80, preferably 10 to 60, mass percent of the lighter aromatics.

Thus the feedstream to the present process generally comprises alkylaromatic hydrocarbons of the general formula $C_6H_{(6-n)}R_n$, where n is an integer from 0 to 5 and each R may be $CH_3$, $C_2H_5$, $C_3H_7$, or $C_4H_9$, in any combination. Suitable alkylaromatic hydrocarbons include, for example but without so limiting the invention, toluene, ortho-xylene, meta-xylene, para-xylene, ethylbenzene, ethyltoluenes, propylbenzenes, tetramethylbenzenes, ethyl-dimethylbenzenes, diethylbenzenes, methylpropylbenzenes, ethylpropylbenzenes, triethylbenzenes, di-isopropylbenzenes, and mixtures thereof. Benzene may also be present, especially where $C_{10}$ aromatic compounds are present and xylenes are a sought product.

Where the sought product is xylenes, the feed stream preferably comprises as the lighter fraction, including toluene and optionally benzene, and as the heavier fraction, at least one $C_9^+$ aromatic compounds. In an embodiment, the molar ratio of benzene and toluene to $C_9^+$ aromatics is from about 0.1:1 to about 10:1, preferably from about 0.3:1 to about 10:1 and even more preferably from about 0.4:1 to about 6:1. A preferred component of the feedstock where the sought product is xylenes is a heavy-aromatics stream comprising $C_9^+$ aromatics. $C_{10}^+$ aromatics also may be present, typically in an amount of 50 mass percent or less of the feed. The heavy-aromatics stream generally comprises at least about 90 mass percent aromatics.

The feedstock is preferably transalkylated in the gas-phase and in the presence of hydrogen. If the feedstock is transalkylated in the gas-phase, then hydrogen is added, commonly in an amount of from about 0.1 moles per mole of alkylaromatics up to 10 moles per mole of total aromatic compounds in the feed. This ratio of hydrogen to aromatic compound is also referred to as hydrogen to hydrocarbon ratio. If the transalkylation is conducted in the liquid phase, it is usually done in a substantial absence of hydrogen beyond what may already be present and dissolved in a typical liquid aromatics feedstock. In the case of partial liquid phase, hydrogen may be added in an amount less than 1 mole per mole of alkylaromatics.

Transalkylation conditions typically comprise elevated temperature, e.g., from about 100° C. to about 540° C., preferably, from about 200° C. to about 500° C. Often, in commercial facilities, the transalkylation temperature is increased to compensate for any decreasing activity of the catalyst. The feed to a transalkylation reaction zone usually first is heated by indirect heat exchange against the effluent of the reaction zone and then is heated to reaction temperature by exchange with a warmer stream, steam or a furnace. The feed then is passed through a reaction zone, which may comprise one or more individual reactors containing catalyst of this invention. The reactors may be of any suitable type and configuration. The use of a single reaction vessel having a fixed cylindrical bed of catalyst is preferred, but other reaction configurations utilizing moving beds of catalyst or radial-flow reactors may be employed if desired.

Transalkylation conditions include pressures ranging from about 100 kPa to about 6 MPa absolute, preferably from about 0.5 to about 5 MPa absolute. The transalkylation reaction can be effected over a wide range of space velocities. The weight hourly space velocity (WHSV) generally is in the range of from about 0.1 to about 20 $hr^{-1}$ preferably from about 0.5 to about 15 $hr^{-1}$, and most often between about 1 to about 5 $hr^{-1}$. Advantageously, the transalkylation is conducted for a time and under other conditions sufficient that at least about 10, preferably at least about 20, and often between about 20 and 60, mole percent of the heavier alkylaromatic, e.g. $C_9^+$ aromatic, is consumed. Preferably, of the heavier alkylaromatics consumed, at least about 70, most preferably at least about 75, mole percent are converted to lower molecular weight aromatics. The preferred transalkylation products are xylenes for a xylene production facility.

The effluent from the transalkylation typically contains, in addition to the transalkylation product, unreacted lighter and heavier aromatics. Co-products such as naphthenes and paraffins will also be present. Typically this effluent is cooled by indirect heat exchange against the feed to the reaction zone and then further cooled through the use of air or cooling water. The effluent may be subjected to distillation in which substantially all $C_5$ and lighter hydrocarbons present in the effluent are provided in an overhead stream and removed from the process. In the same or a different distillation, at least a portion of the unreacted lights are recovered for recycle. A transalkylation product fraction can be withdrawn, and a heavies stream provided. All or a portion of the heavies stream may be recycled to the transalkylation zone. All or a portion of the lighter aromatics can be recycled to the transalkylation zone.

The catalysts of this invention in which rhenium is present in an amount of at least 0.4, preferably at least about 0.7, mass percent based upon the mass of the catalyst, can find use in transalkylating feedstocks containing alkylaromatics of 10 or more carbon atoms due to the enhanced stability of the catalyst. Hence, the feedstock to the transalkylation can contain the bottoms stream from a xylene column which contains predominantly C$_9$ aromatics, but also C$_{10}$ and small amounts of C$_{11}$ and higher alkylaromatics. In such instances, the amount of C$_{10}^+$ aromatics present in the feed may be at least about 5, for example, 5 to 30, mass percent of the total aromatic feed.

In an embodiment, the aromatic feed stream contains polycyclic aromatics. Often the feedstocks have an End Boiling Point of at least about 210° C., preferably at least about 220° C., and sometimes between about 240° to about 280° C. and about 340° to about 360° C. During the transalkylation and in addition to the transalkylation, polycyclic aromatics are converted, with a significant portion, often at least about 50 mole percent, being converted to monocyclic aromatics. Hence, it is possible, in accordance with an aspect of this invention, to convert indanes and naphthalenes, whether or not alkyl substituted, to alkyl substituted monocyclic aromatics. The degradation products of the indane and naphthalene during the conversion to monocyclic aromatics can provide the source of alkyl moieties. Significantly, the processes of this invention enable the conversion of polycyclic aromatics to monocyclic aromatics without undue loss of the monocyclic moieties thus providing high selectivities to the sought monocyclic alkylaromatics.

In an embodiment, the transalkylation conditions are sufficient to provide a transalkylation product End Boiling Point at least about 5° C., more preferably at least about 10° C., lower than that of the feed to the transalkylation. The End Boiling Point is the temperature at which 99.5 mass percent of the sample would have boiled as determined by ASTM Method D2887 simulated distillation GC method.

In an embodiment, the polycyclic aromatics in the feed comprise at least about 0.5, and sometimes at least about 2, for example, between about 5 and about 30, mass percent of the total C$_9^+$ aromatics of the feed stream. Where xylenes are the preferred product, the feed stream preferably contains at least one of benzene and toluene. In another embodiment of the processes of this invention, the feed stream comprises at least a portion of a higher boiling fraction containing C$_9^+$ aromatics such as from a xylene column in a xylene production facility, and the transalkylation is conducted with at least one of benzene and toluene to provide a xylene-containing transalkylation product.

In an embodiment, the processes of this invention comprise contacting a C$_9^+$ aromatic-containing feed stream comprising polycyclic aromatic, often at least one of indane and methyl-substituted indane and naphthalene and methyl substituted naphthalene, with a catalyst comprising a mordenite component; an acidic MFI molecular sieve component having a Si/Al$_2$ molar ratio of less than about 80; a rhenium component ranging from about 0.05 to about 5.0 mass percent of the catalyst; and a rhenium-dispersing binder under transalkylation conditions including the presence of hydrogen to provide a transalkylation product, said contacting being for a time sufficient to convert at least a portion, preferably at least about 25, and most preferably at least about 50, mole percent of the polycyclic aromatic.

Disproportionation

The feedstock for disproportionation comprises alkylaromatic hydrocarbons of the general formula C$_6$H$_{(6-n)}$R$_n$, where n varies from 0 to 5 and R is CH$_3$, C$_2$H$_5$, C$_3$H$_7$, or C$_4$H$_9$, in any combination to obtain more-valuable alkylaromatics. Suitable alkylaromatic hydrocarbons include, for example but without so limiting the invention, toluene, xylenes, ethylbenzene, trimethylbenzenes, ethyltoluenes, propylbenzenes, tetramethylbenzenes, ethyldimethylbenzenes, diethylbenzenes, methylpropylbenzenes, ethylpropylbenzenes, triethylbenzenes, di-isopropylbenzenes, and mixtures thereof.

The feedstock preferably comprises toluene, optionally in combination with C$_9$ aromatics, and suitably is derived from one or a variety of sources. Feedstock may be produced synthetically, for example, from naphtha by catalytic reforming or by pyrolysis followed by hydrotreating to yield an aromatics-rich product. The feedstock may be derived from such product with suitable purity by extraction of aromatic hydrocarbons from a mixture of aromatic and non-aromatic hydrocarbons and fractionation of the extract. The feedstock preferably should contain no more than about 10 mass-% non-aromatics; the content of benzene and C$_8$ aromatics is principally an economic decision relating to the dilution of toluene from these aromatics.

Thus, the invention encompasses processes for the production of xylene such as disproportionation and transalkylation. In an embodiment, the invention comprises contacting a feed stream comprising an aromatic hydrocarbon having at least seven carbon atoms with a catalyst at aromatic conversion conditions including the presence of hydrogen and producing a product stream having an increased concentration of xylene relative to the feed stream wherein the catalyst comprises a mordenite component; an acidic MFI molecular sieve component having a Si/Al$_2$ molar ratio of less than about 80; a rhenium component ranging from about 0.05 to about 5.0 mass percent of the catalyst; and a rhenium-dispersing binder.

A preferred component of the feedstock is a heavy-aromatics stream comprising C$_9$ aromatics, thereby effecting transalkylation of toluene and C$_9$ aromatics to yield additional xylenes. Benzene may also be transalkylated to yield additional toluene. Indane may be present in the heavy-aromatics stream although it is not a desirable component to effect high yields of C$_8$ aromatics product. C$_{10}^+$ aromatics also may be present, preferably in an amount of 30% or less of the feed.

Within the disproportionation process the feed usually is first heated by indirect heat exchange against the effluent of the reaction zone and is then further heated in a fired heater. The resulting vaporous stream is then passed through a reaction zone which may comprise one or more individual reactors. The use of a single reaction vessel having a fixed cylindrical bed of catalyst is preferred, but other reaction configurations utilizing moving beds of catalyst or radial-flow reactors may be employed if desired. Passage of the combined feed through the reaction zone effects the production of a vaporous effluent stream comprising hydrogen and both product and unconverted feed hydrocarbons. This effluent is normally cooled by indirect heat exchange against the stream entering the reaction zone and then further cooled through the use of air or cooling water. The temperature of the effluent stream generally is lowered by heat exchange sufficiently to effect the condensation of substantially all of the feed and product hydrocarbons having six or more carbon atoms per molecule. The resultant mixed-phase stream is passed into a vapor-liquid separator wherein the two phases are separated and from which the hydrogen-rich vapor is recycled to the reaction zone. The condensate from the separator is passed into a stripping column in which substantially all C$_5$ and lighter hydrocarbons present in the effluent are concentrated into an overhead stream and removed from the process. An aromatics-rich stream which is referred to herein as the disproportionation effluent stream is recovered as net stripper bottoms.

Conditions employed in the disproportionation process zone normally include a temperature of from about 200° C. to 600° C., and preferably from about 350° C. to about 575° C.

The temperature required to maintain the desired degree of conversion will increase as the catalyst gradually loses activity during processing. Normal end-of-run temperatures may therefore exceed start-of-run temperatures by 65° C. or more.

The disproportionation zone is generally operated at hydrogen to hydrocarbon ranges about 0.2 to about 0.5. The ratio of hydrogen to hydrocarbon is calculated based on the molar ratio of free hydrogen compared against the feedstock hydrocarbon. Periodic increases in hydrogen to hydrocarbon above 0.5, and preferably in the range of 1 to 5 permit catalyst rejuvenation by hydrogenation of soft coke. In another embodiment, the hydrogen to hydrocarbon ratio ranges from about 1 to about 2 in the disproportionation zone.

The disproportionation zone is operated at moderately elevated pressures broadly ranging from about 100 kPa to 6 MPa absolute. A preferred pressure range is from 2 to 3.5 MPa. The disproportionation reaction can be effected over a wide range of space velocities, with higher space velocities effecting a higher ratio of paraxylene at the expense of conversion. Liquid hourly space velocity generally is in the range of from about 0.2 to 20 $hr^{-1}$.

Xylene Isomerization

The feed stocks to the aromatics isomerization process comprise non-equilibrium xylene and ethylbenzene. These aromatic compounds are in a non-equilibrium mixture, i.e., at least one $C_8$ aromatic isomer is present in a concentration that differs substantially from the equilibrium concentration at isomerization conditions. Thus, a non-equilibrium xylene composition exists where one or two of the xylene isomers are in less than equilibrium proportion with respect to the other xylene isomer or isomers. The xylene in less than equilibrium proportion may be any of the para-, meta- and ortho-isomers. As the demand for para- and ortho-xylenes is greater than that for meta-xylene, usually, the feed stocks will contain meta-xylene. Generally the mixture will have an ethylbenzene content of about 1 to about 60 mass-%, an ortho-xylene content of 0 to about 35 mass-%, a meta-xylene content of about 20 to about 95 mass-% and a para-xylene content of 0 to about 30 mass-%. Usually the non-equilibrium mixture is prepared by removal of para-, ortho- and/or meta-xylene from a fresh $C_8$ aromatic mixture obtained from an aromatics-production process. The feed stocks may contain other components, including, but not limited to naphthenes and acyclic paraffins, as well as higher and lower molecular weight aromatics.

The alkylaromatic hydrocarbons may be used in the present invention as found in appropriate fractions from various refinery petroleum streams, e.g., as individual components or as certain boiling-range fractions obtained by the selective fractionation and distillation of catalytically cracked or reformed hydrocarbons. Concentration of the isomerizable aromatic hydrocarbons is optional; the process of the present invention allows the isomerization of alkylaromatic-containing streams such as catalytic reformate with or without subsequent aromatics extraction to produce specified xylene isomers and particularly to produce para-xylene.

According to the process of the present invention, the feedstock, in the presence of hydrogen, is contacted with the catalyst described herein. Contacting may be effected using the catalyst system in a fixed-bed system, a moving-bed system, a fluidized-bed system, and an ebullated-bed system or in a batch-type operation. In view of the danger of attrition loss of valuable catalysts and of the simpler operation, it is preferred to use a fixed-bed system. In this system, the feed mixture is preheated by suitable heating means to the desired reaction temperature, such as by heat exchange with another stream if necessary, and then passed into an isomerization zone containing catalyst. The isomerization zone may be one or more separate reactors with suitable means therebetween to ensure that the desired isomerization temperature is maintained at the entrance to each zone. The reactants may be contacted with the catalyst bed in upward-, downward-, or radial-flow fashion.

The isomerization is conducted under isomerization conditions including isomerization temperatures generally within the range of about 100° to about 550° C. or more, and preferably in the range from about 150° to about 500° C. The pressure generally is from about 10 kPa to about 5 MPa absolute, preferably from about 100 kPa to about 3 MPa absolute. The isomerization conditions comprise the presence of hydrogen in a hydrogen to hydrocarbon mole ratio of between about 0.5:1 to 6:1, preferably about 1:1 or 2:1 to 5:1. One of the advantages of the processes of this invention is that relatively low partial pressures of hydrogen are still able to provide the sought selectivity and activity of the isomerization and ethylbenzene conversion. A sufficient mass of catalyst (calculated based upon the content of molecular sieve in the catalyst composite) is contained in the isomerization zone to provide a weight hourly space velocity with respect to the liquid feed stream (those components that are normally liquid at STP) of from about 0.1 to 50 $hr^{-1}$, and preferably 0.5 to 25 $hr^{-1}$.

The isomerization conditions may be such that the isomerization is conducted in the liquid, vapor or at least partially vaporous phase. For convenience in hydrogen distribution, the isomerization is preferably conducted in at least partially in the vapor phase. When conducted at least partially in the vaporous phase, the partial pressure of $C_8$ aromatics in the reaction zone is preferably such that at least about 50 mass-% of the $C_8$ aromatics would be expected to be in the vapor phase. Often the isomerization is conducted with essentially all the $C_8$ aromatics being in the vapor phase.

Usually the isomerization conditions are sufficient that at least about 10, preferably between about 20 and 80 or 90, percent of the ethylbenzene in the feed stream is converted. Generally the isomerization conditions do not result in a xylene equilibrium being reached. Often, the mole ratio of xylenes in the product stream is at least about 80, for example, between about 85 and 99, percent of equilibrium under the conditions of the isomerization. Where the isomerization process is to generate para-xylene, e.g., from meta-xylene, the feed stream contains less than 5 mass-% para-xylene and the isomerization product comprises a para-xylene to xylenes mole ratio of between about 0.20:1 to 0.25:1 preferably at least about 0.23:1, and most preferably at least about 0.236:1.

The Catalyst and Preparation

The catalysts of this invention comprise a rhenium component, a molecular sieve component, and a binder. The molecular sieve component comprises MOR and acidic MFI. The mordenite is at least partially in the hydrogen form in the finished catalyst. The MFI is acidic, that is, having a Total Acidity of at least about 0.15, preferably at least about 0.25, and most preferably at least about 0.4, for example, 0.4 to 0.8 as determined by Ammonia Temperature Programmed Desorption (Ammonia TPD). The Total Acidity of the MFI molecular sieve may be that of the MFI to be used in making the catalyst of the invention or may be achieved during the preparation of the catalyst. Typically, the MFI molecular sieve is at least partially in the hydrogen form in the finished catalyst.

The Ammonia TPD process involves first heating a sample (about 250 milligrams) of molecular sieve at a rate of about 5° C. per minute to a temperature of about 550° C. in the presence of a 20 volume percent oxygen in helium atmosphere (flow rate of about 100 milliliters per minute). After a hold of about one hour, helium is used to flush the system (about 15 minutes) and the sample is cooled to about 150° C. The sample is then saturated with pulses of ammonia in helium at about 40 milliliters per minute. The total amount of ammonia used is greatly in excess of the amount required to saturate all the acid sites on the sample. The sample is purged with helium (about 40 milliliters per minute) for about 8 hours to remove physisorbed ammonia. With the helium purge continuing, the temperature is increased at a rate of about 10° C. per minute to a final temperature of 600° C. The amount of ammonia desorbed is monitored using a calibrated thermal conductivity detector. The total amount of ammonia is found by integration. Dividing the total amount of ammonia by the dry weight of the sample yields the Total Acidity. As used herein, values of Total Acidity are given in units of millimoles of ammonia per gram of dry sample.

The mordenite preferably has a $Si/Al_2$ molar ratio of less than about 40:1, preferably less than about 25:1, and most preferably between about 15:1 and 25:1. Often, the preferred mordenites are synthesized with a $Si/Al_2$ molar ratio of between about 10:1 and 20:1. The mordenites may be used as such or may be dealuminated before or after incorporation in the catalyst.

MFI molecular sieves used in the catalysts of this invention have a $Si/Al_2$ molar ratio of less than about 80, preferably less than about 40, more preferably less than about 25, for example, between about 15:1 to about 25:1. The MFI may be used as synthesized or may be dealuminated. Where dealuminated, the activity of the catalyst is enhanced; however, excessive dealumination may result in the transalkylation product containing more benzene co-boilers. While not wishing to be limited by theory, the dealumination may cause some mesoporosity to be introduced into the MFI structure. It is believed that the mesoporosity in the MFI structure can enhance overall conversion.

Dealumination may be effected by any suitable technique such as acid treatment and steaming. Where steamed molecular sieve is used, it is preferably mildly steamed, e.g., using between about 2 and 50, preferably between about 5 to 30, volume percent steam, pressure of from about 100 kPa to 2 MPa, and temperature of less than about 650° C., for example, about 500° C. to about 600° C., more preferably about 550° C. to 600° C. The steam calcination may occur before or after the molecular sieve is shaped into the sought catalyst form, e.g., using a binder. Desirable catalysts have been obtained when the steaming occurs after the formation of the catalyst.

Preferably the mass ratio of MFI to mordenite is in the range of about 1:10 to 5:1, most preferably about 1:10 to 1:1. In an embodiment, the mordenite component comprises between about 20 to about 80 mass percent of the catalyst; the acidic MFI molecular sieve component comprises between about 10 and about 70 mass percent of the catalyst; and the binder comprises between about 1 and about 40 mass percent of the catalyst. In the preferred catalysts of this invention, the catalyst has a MCP Index of at least about 40 mass percent under Evaluation Conditions while exhibiting a Ring Loss of less than 2 mole percent under Evaluation Conditions. Under Evaluation Conditions, the preferred catalysts of this invention provide a product containing less than 10,000, and sometimes less than about 5000, parts per million by mass of total $C_6$ and $C_7$ non-aromatics.

Processing techniques for making the catalyst can affect catalyst performance. For instance, occlusion of catalytically-active sites can occur. Hence, care should be taken, especially where rhenium is provided on the catalyst by impregnation, that the activity of the catalyst is not unduly impaired and that the sought low benzene co-boiler content of the transalkylation product is obtained.

A suitable refractory binder or matrix is used to facilitate fabrication of the catalyst, provide strength and reduce fabrication costs. The binder also provides a surface for dispersion of the rhenium component and, hence, is a rhenium-dispersing binder. Especially where rhenium is provided on the catalyst in a non-ionic or anionic form, an ion exchange mechanism is not available to draw the rhenium into the molecular sieves. Thus, the binder must enable the rhenium to disperse. Suitable binders include inorganic oxides such as one or more of alumina, magnesia, zirconia, chromia, titania, boria, thoria, aluminum phosphate, and zinc oxide. The preferred inorganic oxide binders include alumina, especially transition and gamma aluminas, due to their rhenium dispersing properties. Particularly useful aluminas are commercially available under the trade names Catapal™ B and/or Versal™ 250. Silica typically is not a good rhenium-dispersing binder.

The molecular sieve may be present in a range from 5 to 99 mass percent of the catalyst and the refractory inorganic oxide may be present in a range of from about 1 to 95 mass percent. Preferably, since rhenium is likely present on the binder, the binder is provided in an amount of at least about 5, preferably between about 10 and 40, mass percent of the catalyst.

The molecular sieve component comprises one or more molecular sieves. Molecular sieves include, but are not limited to, BEA, MTW, FAU (including zeolite Y (both cubic and hexagonal forms) and zeolite X), MOR, LTL, ITH, ITW, MEL, FER, TON, MFS, IWW, MFI, EUO, MTT, HEU, CHA, ERI, MWW, and LTA. MFI may be replaced by any suitable alumino-silicate molecular sieve with pores that have at least one 10 member or higher ring. Similarly, MOR may be replaced by any suitable alumino-silicate molecular sieve with pores that have at least one 12 member or higher ring. Furthermore, the pore structure of the molecular sieve can be one or higher dimensional. Molecular sieves of known structure types have been classified according to their three-letter designation by the Structure Commission of the International Zeolite Association (available at the web site www.iza-structure.org/databases) and such codes are used herein. The molecular sieves are preferably at least partially in the hydrogen form in the finished catalyst. The acidity of the molecular sieve may be that of the molecular sieve to be used in making the catalyst of the invention or may be achieved during the preparation of the catalyst.

One shape of the catalyst of the present invention is a cylinder. Such cylinders can be formed using extrusion methods known to the art. Another shape of the catalyst is one having a trilobal or three-leaf clover type of cross section that can be formed by extrusion. Another shape is a sphere that can be formed using oil-dropping methods or other forming methods known to the art.

The catalyst also contains an essential rhenium metal component. This component may exist within the final catalytic composite as a compound such as an oxide or sulfide, in chemical combination with one or more of the other ingredients of the composite. The catalyst may optionally contain additional modifier metal components. Preferred metal modifier components of the catalyst include, for example, tin, germanium, lead, indium, platinum, palladium and mixtures thereof. Preferred modifiers are at least one of tin and germanium. Often the catalysts comprise a catalytically effective amount of acidic molecular sieve, a catalytically effective amount of rhenium, and a combination of tin and germanium wherein the atomic ratio of germanium to rhenium is at least about 2:1 and the atomic ratio of tin to rhenium is at least about 0.1:1. See, for instance, copending patent application Ser. No. 11/460,647, filed on Jul. 28, 2006, now U.S. Pat. No. 7,378,365, herein incorporated in its entirety by reference. The metal components may be incorporated into the catalyst by any means known in the art, such as co-precipitation, ion-exchange, co-mulling or impregnation. A preferred amount is a range of about 0.01 to about 5.0 mass percent on an elemental basis. In an embodiment, the catalyst contains between about 0.05 and about 5.0 mass percent rhenium based upon the total weight of the catalyst, and between about 0.1 and about 3.0 mass percent rhenium in another embodiment. While not wishing to be limited by theory, catalytically effective amounts are those of mordenite for transalkylation, of acidic MFI zeolite for cracking naphthenes, and of rhenium for enhancing overall conversion and catalyst stability at the selected process conditions.

One method of preparing the catalyst involves the utilization of a soluble, decomposable compound containing rhenium to impregnate the carrier material in a relatively uniform manner. Typical rhenium compounds which may be employed include ammonium perrhenate, sodium perrhenate, potassium perrhenate, potassium rhenium oxychloride, potassium hexachlororhenate (IV), rhenium chloride, perrhenic acid, and the like compounds. Preferably, the compound is ammonium perrhenate or perrhenic acid because no extra steps may be needed to remove any co-contaminant species.

Another method for preparing the catalyst comprises co-mulling the molecular sieve component, rhenium and binder to provide an extrudable mixture for forming the sought catalyst shape. Any suitable method for co-mulling technique may be used. In general, the molecular sieve components and binder are blended in dry or dough form. A soluble, decomposable compound containing rhenium is provided in solution with the molecular sieve component prior to or during the blending of the molecular sieve component and binder or after the molecular sieve component and the binder have been blended. Typical rhenium compounds are those set forth above. For the sake of convenience, water is used as the liquid phase of the dough although other liquids could be used. Usually sufficient liquid is added to provide an extrudable mass. Often, an acid is added to peptize the binder.

The mulling may be at any convenient temperature, often in the range of about 5° C. to 90° C. and for a time sufficient to provide the sought uniformity of distribution of the components. The mulling time will vary depending upon the nature of the mixing apparatus and the severity of the mulling. Frequently, the mulling duration is at least about 0.1, for example, about 0.2 to 24, hours. For purposes of avoiding damage to the molecular sieve component, physically milder mulling conditions are used, albeit requiring a longer time to achieve the sought uniformity of distribution of the components. The dough is extruded into the sought catalyst shape and dried, usually at a temperature of between about 50° C. and about 300° C. for about 1 to about 24 hours.

Preferably, whether the catalyst is made by impregnation, co-mulling or other technique, at least one oxidation, or calcination, step is used. It is believed that the calcination step assists in the dispersion of rhenium in the catalyst. The conditions employed to effect the oxidation step are selected to convert substantially all of the metallic components within the catalytic composite to their corresponding oxide form. The oxidation step typically takes place at a temperature of from about 370° C. to about 650° C. An oxygen atmosphere is employed typically comprising air. Generally, the oxidation step will be carried out for a period of from about 0.5 to about 10 hours or more, the exact period of time being that required to convert substantially all of the metallic components to their corresponding oxide form. This time will, of course, vary with the rhenium component used to make the catalyst, the oxidation temperature employed, and the oxygen content of the atmosphere employed. Sometimes steam is present during the calcinations, to modify the acidity and/or pore structure of the molecular sieve, e.g., in an amount of between about 5 and 70, for example, about 5 and 40, volume percent. In any event, the rhenium is preferably in at least a partial oxide form at the time of sulfiding. Usually, the oxidation state of the rhenium at the time of sulfiding is at least about +4.

In preparing the catalyst, a reduction step may be employed. The reduction step may be performed prior to loading the catalytic composite into the hydrocarbon conversion zone (ex-situ reduction) or it may be performed in situ as part of a hydrocarbon conversion process start-up procedure. Good catalyst performance can be obtained without an ex-situ reduction step. If an ex-situ reduction step is employed, it is not essential that substantially all of the metal components be reduced to the corresponding elemental metallic state. For instance, a partial reduction may occur ex situ and additional reduction may occur in situ. It is preferred that the reduction step take place in a substantially water-free environment. Preferably, the reducing gas is substantially pure, dry hydrogen (i.e., less than 20 ppm-mass water). For ex-situ reductions, other gases may be present such as CO, nitrogen, etc. Typically, the reducing gas is contacted with the catalyst at conditions including a reduction temperature of from about 200° C. to about 650° C., often from about 250° C. to 400° C., for a period of time of from about 0.5 to 24 or more hours. The reduction step may be performed under atmospheric pressure or at higher pressures. For in-situ reductions, proper precautions must be taken to pre-dry the conversion unit to a substantially water-free state, and a substantially water-free reducing gas should be employed. Preferably, the reducing gas comprises at least one of hydrogen and a hydrocarbon.

Thus, in an embodiment the invention is a process for making a transalkylation catalyst comprising: a) forming the catalyst comprising a mordenite component, an acidic MFI molecular sieve component having a Si/Al2 molar ratio of less than about 80, a rhenium component ranging from about 0.05 to about 5.0 mass percent of the catalyst, and a rhenium-dispersing binder; b) oxidizing the formed catalyst at conditions including an oxygen atmosphere, a temperature of between 370° C. and about 650° C., and a time of between about 0.5 and about 10 hours; and c) reducing the oxidized catalyst in a reducing gas comprising at least one of hydrogen and a hydrocarbon at conditions including a temperature between about 100° C. and about 650° C.

Preferably, the catalytic composite is subjected to a sulfur treatment or pre-sulfiding step. Where sulfided, the catalysts of this invention may contain higher levels of rhenium than previously found commercially acceptable, thus further enhancing overall conversion and catalyst stability and lifetimes. The sulfided catalysts, for instance, may beneficially have at least about 0.4, for example, about 0.4 to 5.0, mass percent rhenium. The sulfur component may be incorporated into the catalyst by any known technique. Any one or a combination of in situ and/or ex situ sulfur treatment methods is preferred. The resulting catalyst mole ratio of sulfur to rhenium is preferably from about 0.1 to less than about 1.5, and even more preferably the catalyst mole ratio of sulfur to rhenium is about 0.3 to about 0.8. Effective treatment is accomplished by contacting the catalyst with a source of sulfur at a temperature ranging from about 0° C. to about 500° C. The source of sulfur can be contacted with the catalyst directly or via a carrier gas, typically, hydrogen or an inert gas such as nitrogen. In this embodiment, the source of sulfur is typically hydrogen sulfide although other sulfur compounds such as those listed hereinafter can be used.

The catalyst composition can also be sulfided in situ where a source of sulfur is contacted with the catalyst composition by adding it to the hydrocarbon feed stream in a concentration ranging from about 1 ppm-mole sulfur to about 5,000 or 10,000, preferably from about 5 to 500, ppm-mole sulfur. The need to add a sulfur source to the hydrocarbon feed stream may be reduced or eliminated entirely depending on the actual content of sulfur which may already be present in some hydrocarbon streams. Typical examples of appropriate sources of sulfur include hydrogen sulfide, carbon disulfide and alkylsulfides such as methylsulfide, dimethylsulfide, dimethyldisulfide, diethylsulfide and dibutylsulfide. Such sources are exemplary for all sulfiding described herein unless otherwise noted. Typically, sulfur treatment is initiated by incorporating a source of sulfur into the feed and continuing sulfur treatment for a time sufficient to provide the sought amount of sulfiding. Depending upon the concentration of the sulfur in the feed, the sulfiding may be accomplished in less than one hour or may be over a longer period of time, e.g., for a day or more. The sulfur treatment may be monitored by measuring the concentration of sulfur in the product off gas. The time calculated for sulfur treatment will depend on the actual concentration of sulfur in the feed and the desired sulfur loading to be achieved on the catalyst. Especially where sulfiding is done in-situ, good results can be obtained without the need to pre-reduce the catalyst. In some instances it has been found that even when more sulfur is provided than sought for the targeted sulfur to rhenium atomic ratio, the sulfur to rhenium ratio appears to reach a level and the rhenium does not become oversulfided.

In accordance with this invention, it has been found that certain catalyst preparation procedures can enable a rhenium-containing catalyst to be sulfided in a manner that does not adversely affect the performance of other catalyst components, such as molecular sieves, while permitting the use of higher concentrations of rhenium that enhance catalyst stability. The catalysts of this invention are particularly useful for disproportionation and transalkylation of alkylaromatic compounds and for the isomerization of alkylaromatics. The enhanced stabilities exhibited by the catalysts of this invention enable the catalyst to be used for the transalkylation of feeds containing aromatics of 10 and more carbon atoms.

Procedures exemplified for sulfiding rhenium catalysts in the aforementioned patents and published patent applications, while providing acceptable catalysts at low rhenium concentrations, i.e., below about 0.4, and particularly below about 0.25, mass percent rhenium, fail to provide commercially viable catalysts at higher rhenium concentrations. By this invention, it has been found that sulfided rhenium catalyst prepared from catalyst in which the rhenium is partially reduced has enhanced stability and moderated hydrogenation activity even though the concentration of rhenium is greater than 0.4 mass percent. Preferably, the sulfiding is accomplished with a relatively dilute sulfiding atmosphere, e.g., less than about 10,000, and most preferably less than about 1000, parts per million by mole sulfur. Preferably, the sulfiding is done under reducing conditions including a temperature greater than about 100° C., most preferably greater than about 200° C., for example between about 200° C. and 400° C., in the presence of at least one of hydrogen and hydrocarbon, and in the most preferred embodiments, in the presence of carbenium ions.

In an embodiment, the catalysts of this invention comprise a dispersed, selectively sulfided rhenium component on a support comprising a rhenium-dispersing binder, wherein the rhenium (calculated as the elemental metal) is present in an amount of between about 0.05 and 5, preferably 0.4 to 4, mass percent of the catalyst and the atomic ratio of sulfur to rhenium is between about 0.2:1 to 0.7:1, preferably 0.25:1 to 0.5:1. The catalyst further comprises a catalytically effective amount of an acidic molecular sieve.

The preferred catalysts of this invention have been subjected to calcination in the presence of air to enhance dispersion of rhenium on the rhenium-dispersing binder, and are sulfided while rhenium is at least in a partially oxidized state, and most preferably prior to any significant agglomeration of the dispersed rhenium. The bulk oxidation state of the rhenium when sulfiding may be at least +4.

The first sulfiding of the preferred catalysts of this invention are prepared using a highly dilute sulfiding gas under sulfiding conditions. It is believed that the highly dilute gas enhances uniformity of sulfiding of the rhenium in the catalyst. Frequently, the sulfiding is accomplished by passing a sulfur-containing gas over the catalyst, e.g., at a weight hourly space velocity of at least about 0.5 $hr^{-1}$. The sulfiding gas frequently contains less than about 5000, more preferably less than about 500, parts per million by mole (ppm-mole) sulfur.

The preferred catalysts of this invention are first sulfided under reducing conditions comprising a temperature of at least about 100° C., for example, about 200° to 400° C. Reducing conditions may be provided by the presence of at least one of hydrocarbon and hydrogen in the substantial absence of an oxidizing component such as molecular oxygen, nitrogen dioxide, or the like. In some instances, sulfiding under pressure is desired, e.g., between about 0.1 to 10 MPa gauge. Often the partial pressure of hydrogen during sulfiding is at least about 0.02, say, about 0.04 to 10 MPa.

Further preferred catalysts of this invention are first sulfided in the presence of carbenium ions. As carbenium ions are intermediate chemical reaction products, the most convenient mode of introducing carbenium ions is to effect hydrocarbon cracking during the sulfiding. The hydrocarbon may be any suitable compound capable of being cracked at the conditions of sulfiding, and especially suitable hydrocarbons comprise ethylbenzene, methylethylbenzene and propylbenzene. Especially where the catalyst comprises an acidic molecular sieve, carbenium ions may readily be generated. Cracking may occur in the range of about 250° C. to 500° C., with 250° C. to 400° C. being preferred for sulfiding. Where the rhenium-containing catalyst has insufficient cracking activity, higher temperatures may be required. Preferably the sulfiding is accomplished by passing a gas comprising the sulfiding component and the hydrocarbon for generating carbenium ions over the catalyst. Hydrogen is also present. The sulfiding gas frequently contains less than about 5000, more preferably less than about 500, parts per million by mole (ppm-mole) sulfur. The gas also contains at least about 2, preferably from about 5 to 99, mole percent of the hydrocarbon capable of generating the carbenium ions. The balance of the gas may be hydrogen and other hydrocarbons. Generally, hydrogen is present in a mole ratio to hydrocarbon of about 1:1 to 10:1.

The sulfiding is typically accomplished such that about 0.2 to 0.7, preferably 0.25 to 0.5, atoms of sulfur are provided per atom of rhenium. Where the catalyst comprises other components that can sorb or react with sulfur, the total amount of sulfur provided should be sufficient to assure that the sought amount of sulfur for the rhenium is provided. The sulfided catalysts of this invention exhibit attenuated hydrogenation activity. Accordingly, greater amounts of rhenium can be used than heretofore possible to obtain enhanced stability without undue hydrogenation activity. In most instances, the catalysts, once prepared, need not be further sulfided during normal operation. Process upsets or oxidative regenerations may necessitate resulfiding.

The invention also pertains to processes for making sulfided, rhenium-containing catalysts. In one aspect, these processes comprise providing catalyst having a dispersion of rhenium on a support comprising a rhenium-dispersing binder and an essential absence of sulfur; and contacting the catalyst with a gas containing sulfur while the rhenium is in at least a partially oxidized state.

The catalysts of this invention are particularly useful for xylene isomerization, toluene disproportionation to xylenes and benzene, and transalkylation of aromatics with 9 or more carbon atoms with at least one of toluene and benzene to produce xylenes. The catalysts are attractive for converting ethylbenzene to benzene and the dealkylation of ethyl and higher alkyl groups of alkylbenzenes such as methyl ethyl benzene. The catalyst are also attractive for converting non-aromatics, for example, to saturate and/or crack non-aromatics. Feedstocks for xylene isomerization can contain ethylbenzene, for example, between about 5 and 60 mass percent, and ethylbenzene can be converted. Advantageously, the attenuated hydrogenation activity of the catalysts of this invention results in reduced Ring Loss while achieving desired conversions of feedstock.

In some instances, the calcined catalyst is partially reduced prior to or during sulfiding. The amount of reduction is a function of the reducing atmosphere, the temperature of the reduction and the duration of the reduction. Under excessive reducing conditions, especially those involving higher temperature, the dispersion of rhenium in the catalyst can be adversely affected. Where a reduction precedes sulfiding, the reducing temperature is less than about 400° C., preferably in the range of about 100° C. to 350° C. The duration of the reduction is preferably such that undue agglomeration of the rhenium on the catalyst does not occur and, preferably, such that the rhenium has an oxidation state of at least about +4. Thus, the reduction is typically conducted for a period of less than about 24 hours, with shorter periods being used at higher temperatures. For instance, at 280° C., the duration of the reduction is preferably less than about 12 hours.

The sulfiding may occur simultaneously with at least a portion of the reduction or subsequent to the reduction. Preferably, the sulfiding occurs under reducing conditions. The reducing conditions preferably should not be so severe that substantially all of the metal components are converted to the corresponding elemental metallic state. It is preferred that the reduction take place in a substantially water-free environment. Preferably, the reducing gas is substantially pure, dry hydrogen (i.e., less than 20 ppm-mass water). However, other gases may be present such as hydrocarbon, CO, nitrogen, etc. The reduction step may be performed under atmospheric pressure or at higher pressures. The preferred pressures are from about 50 kPa (absolute) to 10 MKa (absolute), and often in the range of 200 to 5000 kPa (absolute).

Where the sulfiding is conducted under reducing conditions, the reducing gas will contain a sulfiding component. The sulfur component may be incorporated into the catalyst by any known technique. Any one or a combination of in situ and/or ex situ sulfur treatment methods is preferred. Effective treatment is accomplished by contacting the catalyst with a source of sulfur at a temperature ranging from about 0° C. to about 500° C. The source of sulfur can be contacted with the catalyst directly or via a carrier gas, typically, a gas such as hydrogen or nitrogen. In this embodiment, the source of sulfur is typically hydrogen sulfide although sources can be used.

In the event that the catalysts of this invention are regenerated by calcination, often resulfiding is beneficial. Regeneration conditions generally comprise the controlled carbon burn-off of carbonaceous deposits on the catalyst in an oxygen-containing atmosphere, e.g., air or air with additional nitrogen and/or steam, at temperatures ranging from between about 370° C. to 650° C. for a period of between about 0.5 and 24 hours. In an embodiment, the carbon burn-off period may be from about 7 to about 14 days. Carbonaceous deposits are burned off and rhenium may be redispersed. The oxidation state of rhenium may also be increased as well as being converted to an oxide. The resulfiding can conveniently be conducted in the modes set forth above.

EXAMPLES

In the following examples, all parts and percentages of liquids and solids are by mass and those of gases are molar, unless otherwise stated or apparent from the context. The following examples are illustrative only and are not in limitation of the broad aspects of the invention.

Catalyst Preparation

The following general preparation is used to make catalysts of this invention: A powder blend of alumina (commercially available under the trade name Catapal™ B), mordenite (ammonium form and synthesized to a $Si/Al_2$ molar ratio of about 18:1) in mass ratios corresponding to those sought in the final catalyst are added to a muller and mixed. The duration of dry mulling is not critical provided that an essentially uniform admixture is produced. Often, a uniform admixture can be formed in about 30 minutes. A liquid mixture comprising nitric acid (69.5 mass percent $HNO_3$), deionized water and ammonium perrhenate is added to the dry admixture while continuing the mulling. The mass of the liquid added (excluding the mass of ammonium perrhenate) is about 0.113 grams per gram of dry mix. The mass of ammonium perrhenate contained in the liquid mixture is that sufficient to provide the sought concentration of rhenium in the catalyst. The mulling is continued for about 15 to 30 minutes and additional distilled water is added to provide a dough having an LOI of about 40 mass percent. The mulling is continued until the mull is semi-broken with small agglomerates and the ability to form a mass when squeezed by hand. The dough is extruded through a die plate to form cylindrically shaped (0.16 cm diameter) extrudate particles.

Catalyst A is substantially prepared by the foregoing procedure using ratios of components such that the catalyst nominally contains 70 mass percent MOR, 15 mass percent MFI ($Si/Al_2$ molar ratio=23:1), balance alumina and 0.15 mass percent rhenium (calculated as the metal). The extrudate particles are then dried in air at about 100° C. for about one hour and calcined in air at about 580° C. for about 6 hours. About four of these six hours are used heating to and cooling from this peak temperature.

Catalyst B is substantially prepared by the foregoing procedure using ratios of components such that the catalyst nominally contains 70 mass percent MOR, 15 mass percent MFI ($Si/Al_2$ molar ratio=38:1), balance alumina and 0.15 mass percent rhenium (calculated as the metal). The extrudate particles are then dried in air at about 100° C. for about one hour and calcined in air at about 580° C. for about 6 hours. About four of these six hours are used heating to and cooling from this peak temperature.

Catalyst C is substantially prepared by the foregoing procedure using ratios of components such that the catalyst nominally contains 50 mass percent MOR, 25 mass percent MFI (Si/Al$_2$ molar ratio=23:1), balance alumina and 0.15 mass percent rhenium (calculated as the metal). The extrudate particles are then dried in air at about 100° C. for about one hour and calcined in air at about 580° C. for about 6 hours. About four of these six hours are used heating to and cooling from this peak temperature.

Catalyst D is substantially prepared by the foregoing procedure using ratios of components such that the catalyst nominally contains 50 mass percent MOR, 25 mass percent MFI (Si/Al$_2$ molar ratio=38:1), balance alumina and 0.15 mass percent rhenium (calculated as the metal). The extrudate particles are then dried in air at about 100° C. for about one hour and calcined in air containing 25 volume percent steam at about 580° C. for about 6 hours. About four of these six hours are used heating to and cooling from this peak temperature.

Catalyst E is substantially prepared by the foregoing procedure using ratios of components such that the catalyst nominally contains 50 mass percent MOR, 25 mass percent MFI (Si/Al$_2$ molar ratio=23:1), balance alumina and 1.0 mass percent rhenium (calculated as the metal). The extrudate particles are then dried in air at about 100° C. for about one hour and calcined in air at about 580° C. for about 6 hours. About four of these six hours are used heating to and cooling from this peak temperature.

Catalyst F is a portion of Catalyst E that is reduced in hydrogen at 500° C. for 12 hours, cooled to room temperature while being retained in a nitrogen atmosphere, and sulfided at room temperature by injecting hydrogen sulfide into the nitrogen atmosphere surrounding the catalyst. The amount of hydrogen sulfide injected is that calculated to provide 0.5 atom of sulfur per atom of rhenium. It is believed that the actual amount of sulfur on the catalyst is less than that expected.

Catalyst G is a portion of Catalyst E that is reduced in hydrogen at 500° C. for 12 hours and cooled to room temperature while being retained in a nitrogen atmosphere.

Catalyst H is a portion of Catalyst E that is reduced in hydrogen at 280° C. for 12 hours and cooled to room temperature while being retained in a nitrogen atmosphere.

Catalyst I is a portion of Catalyst E that is reduced in hydrogen at 280° C. for 12 hours, cooled to room temperature while being retained in a nitrogen atmosphere, and sulfided at room temperature by injecting hydrogen sulfide into the nitrogen atmosphere surrounding the catalyst. The amount of hydrogen sulfide injected is that calculated to provide 0.5 atom of sulfur per atom of rhenium. It is believed that the actual amount of sulfur on the catalyst is less than that expected.

Example 1

Catalysts A through D are evaluated in a pilot plant for transalkylation catalytic activity. The catalysts are pre-conditioned in the pilot plant by maintaining the catalyst at 280° C. for 5 to 6 hours in the presence of dry hydrogen. The feed for the activity screening comprises 49.9 volume percent toluene and 40.0 volume percent of alkylaromatics having 9 carbons, with the balance being predominantly alkylaromatics of 10 carbon atoms, and sufficient hydrogen to provide a hydrogen to hydrocarbon mole ratio of about 4. The feed rate is sufficient to provide a weight hourly space velocity of about 4 hr$^{-1}$. The pilot plant is at about 2760 kPa gauge and at a temperature sufficient to provide about 50 mass percent conversion of the aromatics. The reported performance parameters are at 50 percent conversion of the feed; however, where the conversion varies from the target, the parameter values reported are those derived by interpolation to 50 percent conversion. The Table I summarizes the results. In the table, WABT is weight average bed temperature, Xylene Yield is the mass percent of xylene in the transalkylation product, and Benzene Co-Boilers is ppm-mass of the total non-aromatics having 6 and 7 carbon atoms per mass unit of benzene in the transalkylation product. All values are taken at the point that the catalyst has been contacted with about 72 liters of feed per kilogram of catalyst.

TABLE I

| Catalyst | WABT, ° C. | Xylene Yield, mass percent | Ring Loss, mole percent | Benzene Co-boilers, ppm-mass |
|---|---|---|---|---|
| A | 395 | 27.5 | 2.4 | 3000 |
| B | 385 | 27.6 | 2.4 | 5000 |
| C | 395 | 26.7 | 3.1 | 1000 |
| D | 380 | 29.1 | 2.4 | 2300 |

Example 2

Catalysts E to I are evaluated in a different pilot plant having the capability for co-feeding a sulfur compound. The high rhenium loading on the catalyst would, in the absence of sulfiding, render the catalyst unsuitable for transalkylation due to high Ring Loss and xylene loss. The catalysts are pre-conditioned in the pilot plant by maintaining the catalyst at 280° C. for 5 to 6 hours in the presence of dry hydrogen. The feed for the activity screening comprises 49.9 volume percent toluene and 40.0 volume percent of alkylaromatics having 9 carbons, with the balance being predominantly alkylaromatics of 10 carbon atoms, and sufficient hydrogen to provide a hydrogen to hydrocarbon mole ratio of about 4:1.

The feed rate is sufficient to provide a weight hourly space velocity of about 4 hr$^{-1}$. The pilot plant is at about 2760 kPa gauge and at a temperature targeted to provide about 50 mass percent conversion of the aromatics in the feed. In some of the runs, sulfur is co-fed as dimethyldisulfide in an amount of 150 ppm-mole of the feed. The duration of this feeding is sufficient to provide about 0.5 atom of sulfur per atom of rhenium in the catalyst. The lined-out performance of the catalyst during the run is reported in Table II. The reported performance parameters are at 50 percent conversion of the feed; however, where the conversion varies from the target, the parameter values reported are those derived by interpolation to 50 percent conversion. In the table, WABT is weight average bed temperature, Xylene Yield is the mass percent of xylene in the transalkylation product, and Benzene Co-boilers is ppm-mass of the total non-aromatics having 6 and 7 carbon atoms per mass unit of benzene in the transalkylation product. SOR is start of run.

TABLE II

| Catalyst | DMDS | WABT, ° C. | Xylene Yield, mass percent | Ring Loss, mole percent | Benzene Co-boilers, ppm-mass |
|---|---|---|---|---|---|
| Run I E | SOR | 369 | 28.7 | 1.8 | 9000 |
| Run II F | None | 358 | 27.6 | 3.3 | 60000 |
| Run III F | SOR | 354 | 27.6 | 3.3 | 55000 |
|  | @50 l/kg | 362 | 27.4 | 3.3 | 45000 |

TABLE II-continued

| Catalyst | DMDS | WABT, °C. | Xylene Yield, mass percent | Ring Loss, mole percent | Benzene Co-boilers, ppm-mass |
|---|---|---|---|---|---|
| Run IV G | SOR | 353 | 27.2 | 4.6 | 110000 |
| | @58 l/kg | 362 | 27.5 | 3.3 | 40000 |
| | @94 l/kg | 364 | 27.5 | 3.2 | 35000 |
| Run V G | SOR 2X | 360 | 27.7 | 3.0 | 40000 |
| | @94 l/kg | 364 | 27.8 | 2.9 | 35000 |
| Run VI H | SOR | 365 | 28.3 | 2.5 | 25000 |
| Run VII I | None | 362 | 28.2 | 2.8 | 35000 |
| | @86 l/kg | 364 | 27.9 | 2.9 | 35000 |

Catalysts F and G, which are reduced at 500° C., do not exhibit the high xylene yield and low Ring Loss achievable by Catalyst E which is only subjected to reducing conditions by the pretreatment at 280° C. for 5 to 6 hours. Catalyst E also exhibits low benzene co-boiler production. Regardless whether these Catalysts F and G are sulfided ex situ or in situ, their performance does not achieve that of Catalyst E.

In Run IV, Catalyst G, which is also reduced at 500° C., but not ex situ sulfided as is Catalyst F, is sulfided in situ at start-up. The sulfiding, however, fails to achieve a low Ring Loss and high benzene purity of Catalyst E. Additional sulfidings result in an improvement in benzene purity, but again, the performance of Catalyst E is not obtained. See Run V in which Catalyst G is sulfided twice at the beginning of the run. The double sulfiding provides a performance with less Ring Loss and lower benzene co-boiler make than in Run IV. However, as with Catalyst G in Run IV, the effect of the sulfiding does not provide a catalyst performance comparable to Catalyst E.

Catalysts H and I are subjected to pre-reduction, but at a lower temperature than that used to make Catalysts F and G. The total duration of reduction prior to sulfiding, however, is greater than that for Catalyst E. While still within the broad aspects of the invention, these Catalysts evidence benefits with less severe reductions and with the initial sulfiding being under reducing conditions. The data are indicative that differing sulfiding mechanisms exist that can provide much differing catalyst performances.

The invention claimed is:

1. A process for producing xylene, the process comprising: contacting a feed stream comprising an aromatic hydrocarbon having at least seven carbon atoms with a catalyst at aromatic conversion conditions including the presence of hydrogen comprising at least one of a transalkylation reaction, disproportionation reaction, and isomerization reaction and producing a product stream having an increased concentration of xylene relative to the feedstream wherein the catalyst comprises a mordenite component; an acidic MFI molecular sieve component having a $Si/Al_2$ molar ratio of less than about 40; a rhenium component ranging from about 0.05 to about 5 mass percent of the catalyst; and a rhenium-dispersing binder.

2. The process of claim 1 wherein the $Si/Al_2$ molar ratio of the acidic MFI molecular sieve component is less than about 25.

3. The process of claim 1 wherein the $Si/Al_2$ molar ratio of the mordenite component is less than about 40.

4. The process of claim 1 wherein the binder comprises alumina.

5. The process of claim 1 wherein the catalyst further comprises a sulfur component.

6. The process of claim 5 wherein the atomic ratio of sulfur to rhenium is between about 0.2:1 and about 0.7:1.

7. The process of claim 5 wherein the rhenium component is present in an amount between about 0.4 and about 5 mass percent of the catalyst.

8. The process of claim 1 wherein the acidic MFI molecular sieve component has a Total Acidity of at least about 0.25.

9. The process of claim 1 wherein the mass ratio of the acidic MFI molecular sieve component to the mordenite component is in the range of about 1:10 to 5:1.

10. The process of claim 1 wherein the acidic MFI molecular sieve component is a steamed MFI molecular sieve.

11. The process of claim 1 wherein the mordenite component comprises between about 20 to about 80 mass percent of the catalyst; the acidic MFI molecular sieve component comprises between about 10 and about 70 mass percent of the catalyst; and the binder comprises between about 1 and about 40 mass percent of the catalyst.

12. The process of claim 1 wherein the feed comprises toluene and wherein the aromatic conversion conditions are toluene disproportionation conditions; the process further comprising a temperature ranging from 200° C. to about 600° C., a hydrogen to hydrocarbon mole ratio ranging from about 0.2 to about 0.5, a pressure ranging from about 100 kPa to about 6 MPa absolute, and a weight hourly space velocity (WHSV) ranging from about 0.2 $hr^{-1}$ to about 20 $hr^{-1}$.

13. The process of claim 1 wherein the aromatic conversion conditions are transalkylation conditions; the process further comprising a temperature ranging from 100° C. to about 540° C., a pressure ranging from about 100 kPa to about 6 MPa absolute, and a weight hourly space velocity (WHSV) ranging from about 0.1 $hr^{-1}$ to about 20 $hr^{-1}$.

14. The process of claim 13 wherein the feed stream has an Ending Boiling Point of at least about 210° C.

15. The process of claim 14 wherein the product stream has an Ending Boiling Point at least 10° C. lower than that of the feed stream.

16. The process of claim 13 wherein the feed stream comprises $C_9^+$ aromatics.

17. The process of claim 16 wherein the feed stream further comprises at least one of benzene and toluene.

18. The process of claim 16 wherein the feed stream comprises between about 5 and about 30 mass percent of $C_{10}^+$ aromatics.

19. The process of claim 16 wherein at least about 0.5 mass percent of the total $C_9^+$ aromatics in the feed stream are polycyclic aromatics.

20. The process of claim 16 wherein at least about 20 mole percent of the total $C_9^+$ aromatics in the feed stream are consumed and at least about 70 mole percent of the consumed $C_9^+$ aromatics are converted to aromatics having a lower molecular weight.

* * * * *